(12) United States Patent
Alfano et al.

(10) Patent No.: US 9,804,088 B2
(45) Date of Patent: Oct. 31, 2017

(54) SPATIAL FREQUENCY SPECTROMETER FOR AND METHOD OF DETECTION OF SPATIAL STRUCTURES IN MATERIALS

(71) Applicants: Robert R. Alfano, Bronx, NY (US); Yang Pu, Irvine, CA (US)

(72) Inventors: Robert R. Alfano, Bronx, NY (US); Yang Pu, Irvine, CA (US)

(*) Notice: Subject to any disclaimer, the term of this patent is extended or adjusted under 35 U.S.C. 154(b) by 44 days.

(21) Appl. No.: 14/580,892

(22) Filed: Dec. 23, 2014

(65) Prior Publication Data

US 2015/0176968 A1    Jun. 25, 2015

Related U.S. Application Data

(60) Provisional application No. 61/964,096, filed on Dec. 23, 2013.

(51) Int. Cl.
*G01B 9/02* (2006.01)
*G01N 21/47* (2006.01)

(52) U.S. Cl.
CPC .............................. *G01N 21/4788* (2013.01)

(58) Field of Classification Search
CPC .......... G01N 21/4788; G01N 21/9501; G01N 21/4795; G01N 2201/1293; G01N 30/8631; G01N 21/6428; G01N 21/6458; G01N 21/65; G01B 9/02091; G01B 9/02044; G01B 9/02004; G01B 9/02041; G01B 9/02084; G01B 9/02043; G01B 9/021; G01B 11/14; G01B 11/16; G01B 9/0209; G01B 9/02002; G01B 9/02032; G07G 1/0045; G07G 1/0036; G07G 3/00; G07G 3/006; G07G 1/0054
See application file for complete search history.

(56) References Cited

U.S. PATENT DOCUMENTS

| 5,627,678 A * | 5/1997 | Nishii | G02B 27/46 359/559 |
| 8,248,617 B2 * | 8/2012 | De Groot | G03F 7/70633 356/508 |

(Continued)

OTHER PUBLICATIONS http://physics.cancer.gov/research/2014/jan/po_news_a.aspx.*

(Continued)

*Primary Examiner* — Tarifur Chowdhury
*Assistant Examiner* — Mohamed K Amara
(74) *Attorney, Agent, or Firm* — Myron Greenspan; Lackenbach Siegel LLP

(57) ABSTRACT

Spatial frequency spectra from periodic, aperiodic and quasi-random structures in materials are shown and used to detect differences among objects via internal coding from the spatial frequencies. The method is applied to different grades of human tissues for a new form of histology and pathology, and to detect art forgeries and coding boxes, money and papers and gems. The randomness of material structures on surface and at depths near surface can be detected from the spatial spectrum. In tissue spectral features from normal to different stages of cancer in tissue for ex vivo and in vivo applications can be recognized by different spectral fingerprints content of the spatial frequency. Similarly, the painting for the strokes of artist is different. A new type of instrument is described to analyze materials as a Spatial Frequency Spectrometer.

22 Claims, 8 Drawing Sheets

(56) References Cited

U.S. PATENT DOCUMENTS

| | | | | |
|---|---|---|---|---|
| 9,332,902 B2* | 5/2016 | Tumlinson | ............. | A61B 3/102 |
| 2005/0018180 A1* | 1/2005 | Ayres | .................. | G01M 11/005 356/237.1 |
| 2008/0002209 A1* | 1/2008 | Yaqoob | ............. | G01B 9/02004 356/490 |
| 2008/0215271 A1* | 9/2008 | Bankhead | ............ | G01B 11/026 702/71 |
| 2013/0010283 A1* | 1/2013 | Villiger | .................. | G01J 3/453 356/72 |
| 2013/0135614 A1* | 5/2013 | Wax | ....................... | G01N 21/49 356/300 |
| 2013/0169969 A1* | 7/2013 | Popescu | ............. | G01B 9/02091 356/450 |

OTHER PUBLICATIONS

Chandra S. Yelleswarapu et al. ("Optical Fourier techniques for medical image processing and phase contrast imaging", Opt. Comm, 281(7) 2008, pp. 1876-1888).*

Joseph Goodman, "Introduction to Fourier Optics, Third Edition," Roberts & Company, ISBN 0-9747077-2-4, Copyright @ 2005.

Barbara Hoffman, John Schorge, Joseph Schaffer, Lisa Halvorson, Karen Bradshaw, F. Cunningham, "Williams Gynecology, Second Edition," McGraw-Hill Professional, ISBN 978-0-07-171672-7, Copyright @ 2012.

Jaidip Jagtap, Pankaj Singh, Chayanika Pantola, Asha Agarwal, Kiran Pandey, Asima Pradhan, "Study and discrimination of human cervical tissue images through multifractal analysis,".

Yang Pu, W. B. Wang, Yuanlong Yang, and R. R. Alfano, "Stokes shift spectroscopy highlights differences of cancerous and normal human tissues," Opt. Lett., 37(16), 3360-3362 (2012).

Nick Efford, "Digital Image Processing: A Practical Introduction Using JavaTM," Pearson Education, Addison-Wesley, ISBN-13: 9780201596236, Copyright © 2000 [6] B. E. A. Saleh and M.. C. Teich, "Fundamentals of Photonics, Chapter 2, Fourier Optics," John Wiley & Sons, Inc., ISBN 978-0-471-35832-9, Copyright @ 2007.

B. E. A. Saleh and M.. C. Teich, "Fundamentals of Photonics, Chapter 2, Fourier Optics," John Wiley & Sons, Inc., ISBN 978-0-471-35832-9, Copyright @ 2007 [7] S. Alexandrov, S. Uttam, R. K. Bista, Y. Liu, "Spectral encoding of spatial frequency approach for characterization of nanoscale structures," Appl Phys Lett., 101(4), 033702 (2012).

S. Alexandrov, S. Uttam, R. K. Bista, Y. Liu, "Spectral encoding of spatial frequency approach for characterization of nanoscale structures," Appl Phys Lett., 101(4), 033702 (2012).

S. Chung, G. Legge, and B. Tjan, "Spatial-frequency characteristics of letter identification in central and peripheral vision," Vision Res., 42(18), 2137-152 (2002).

L. Cherkezyan, H. Subramanian, V. Stoyneva, J. Rogers, S. Yang, D. Damania, A. Taflove, V. Backman, "Targeted alteration of real and imaginary refractive index of biological cells by histological staining," Opt. Lett., 37(10), 1601-1603 (2012).

* cited by examiner

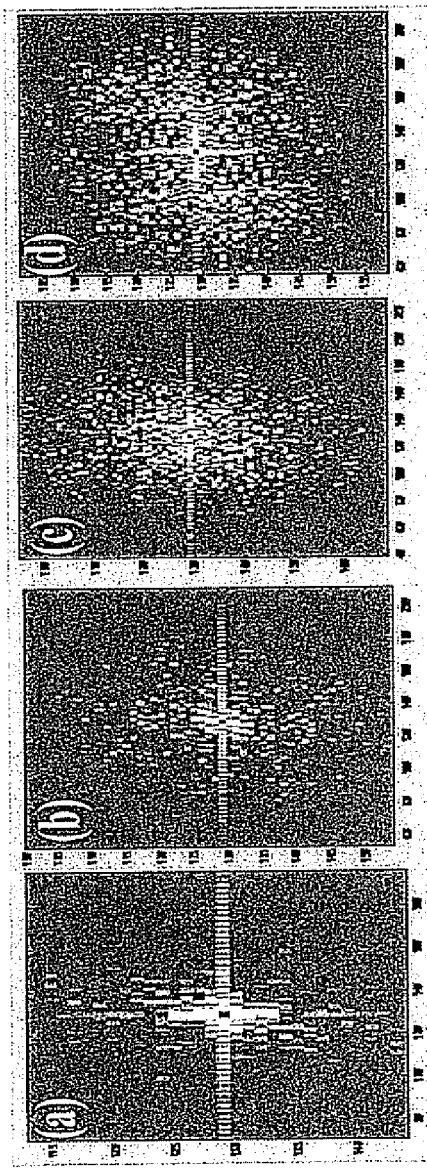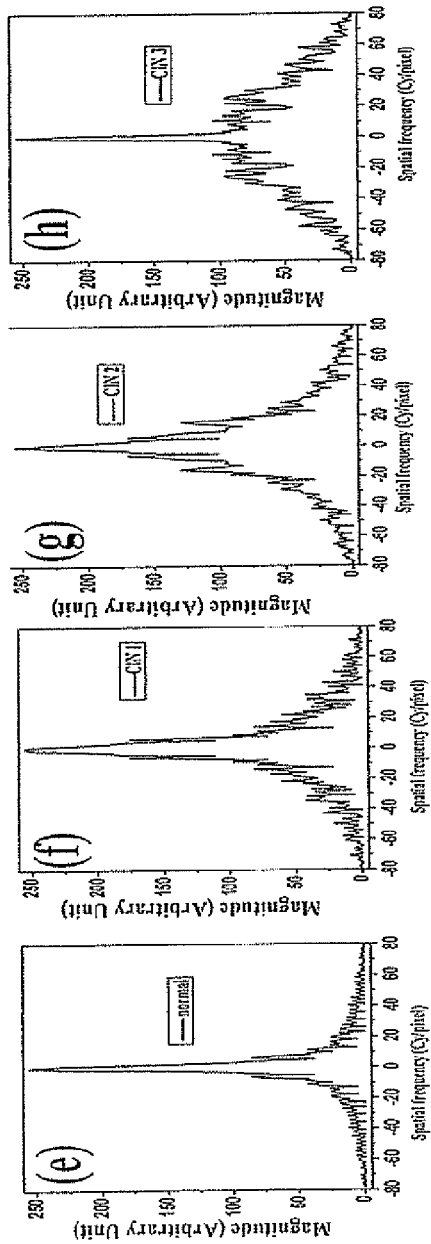
FIG. 4(a) FIG 4(b) FIG. 4(c) FIG. 4(d)
FIG. 4(e) FIG. 4(f) FIG. 4(g) FIG. 4(h)

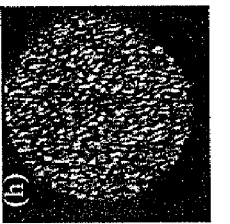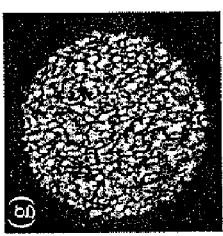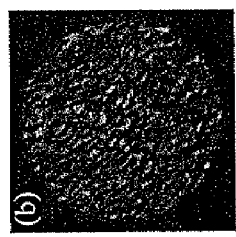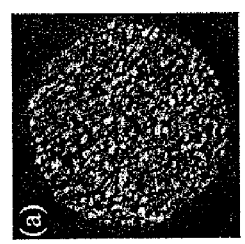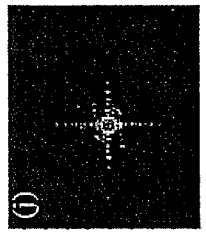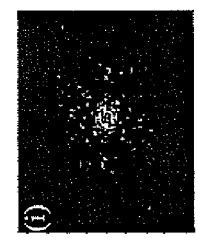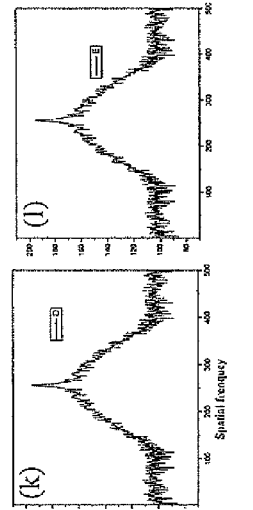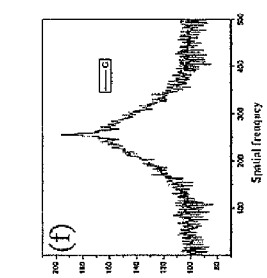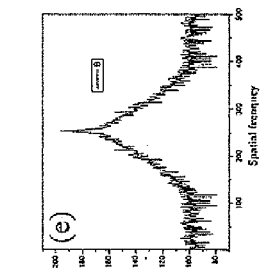

SPATIAL FREQUENCY SPECTROMETER FOR AND METHOD OF DETECTION OF SPATIAL STRUCTURES IN MATERIALS

BACKGROUND OF THE INVENTION

1. Field of the Invention

The invention generally relates to method of and apparatus for obtaining fingerprint information about structures of materials and, more specifically using a spatial frequency spectrometer for and method of detection of spatial structures in materials.

2. Description of the Prior Art

Spatial frequency spectrum may be considered to be able to yield fingerprint information about the surface and internal structures of samples. It can provide spatial information from the periodic, aperiodic, and random structures of the sample from the spatial intensity distribution. A spatial spectrum can be formed given the dominating spatial variation within and on the surface the material. Here, we teach the use of spatial frequency to form a spectrum to obtain information on the internal structure of materials such as tissues-human and animal state, paper goods as money, mail, gems (diamonds defects and quality), and art forms to form a spatial spectrum of a material form in $cm^{-1}$. The spatial spectrum can yield spatial coherent information from the periodic and random structures of the material. It is well known that a focal-Fourier plane with light intensity distribution is composed of "spatial frequencies" which is similar as the way that a time domain signal is composed of various frequencies [1]. The spatial frequency can be obtained by a Fourier transform analysis of the light intensity distribution which and how many frequencies are contained in the waveform in terms of spatial frequencies for unit of cycles (cy) per unit distance ($cm^{-1}$). These frequencies can be addressed by Fourier decomposition, which is analogous to temporal frequencies in cycles per second for in time-domain. The light can arise from elastic scatter, fluorescence, and Raman images of the material. The teachings laid down the foundation for a Spatial Frequency Spectrometer to determine the emitting spatial structure of the material.

An example of the spatial spectrum of a material is the comparing different tissue types. Tissue can be normal, benign, dysplastic (precancer) and cancers. Spatial frequency can reveal the different states. Cervical dysplasia, e.g. Cervical Intraepithelial Neoplasia (CIN), is the potentially premalignant and abnormal squamous cells on surface of cervix [2]. Although not a cancer, above 12% of CIN cases progress to become cervical cancer if left untreated [2]. Others cause warts. Cellular changes and disorder of tissue structure are associated with the stages of CIN, which is classified in three grades [2]. Usually cervical tissue has order and well-defined cell structure in its normal stage [2]. When cancer starts, the tissue becomes distorted, random, and structure-reducing. The current techniques for CIN include the Papanicolaou or "Pap" smear and colposcopy. However, to make a definite diagnosis of cervical dysplasia, a biopsy should be taken of any abnormal appearing areas [2]. The different types of skin cancer from ABCD can be revealed in the spatial frequencies from the structures of melanoma and basal carcinomas.

Another example for spatial frequencies where structures are apparent is in paintings. A paint of different artist strokes are different and can be used to show different characteristic spatial frequency pattern with unique spatial patterns. Also, different artist paintings can show how painter strokes (right handed and left hand) can be detected as a second example on the use of spatial structure. The salient properties associated with light and photonic laser technology in the visible-NIR can be used to locate these blind blisters so that the difference areas can be identified between the art of a masterpiece and forgery art form and from the spatial frequencies in the spectrum.

Photonic measurements and images from scatter and emission processes can be used in the visible-NIR using the ultimate light called the Supercontinuum, lamps, LEDs and lasers and spatial frequency to scan the surface of paintings and other textured art works to determine if the brushworks or the signatures are by the original artist. We also know that this Photonic technology will detect areas that may be over-painted either by the artist or in an earlier restoration. There are spatial variations in paper on nm scale from fibers, different currency and denominations have native or intrinsic spatial variations and can be implanted with a spatial code within. Diamonds have defects that can provide a code for a stone or gem.

SUMMARY

An innovative approach is disclosed to use spatial frequencies of images and spatial frequency to characterize materials such as tissue, art forms, paper goods, and defects in gems, from their scattering of light, fluorescent and/or Raman images to distinguish materials. For example, in tissue changing among normal and different stages of dysplasia tissues. Since spatial frequency spectra provide information of the periodic and random structures of two dimensional (2D) light intensity distribution and since the periodic structure of collagen in the stromal region of tissue gets disordered [2-4] with progress in the grade of CIN, the spatial frequency spectra of these tissues may offer new diagnostic ways to analyze the stages from normal, dysplasia to full cancer.

Two artist paintings will be used to show structure of light scattered that create optical vortices and different spatial frequencies. The backscattered pulses will be computed for comparison with experimental data. The backscattered light from discrete random media has been found to exhibit the phenomenon of weak localization, which arises from the coherent interference between the scattered light and its time-reversed counterpart in the random medium. This interference enhances the intensity of the light scattered in the backward direction within a small angular spread. In the exact backward direction the intensity of the scattered light is nearly twice the diffuse intensity. The intensity decreases to a constant value (equal to diffuse intensity) as the angle of the scattered light increases. The profile of the angular distribution of scattered light intensity about the backward direction, known as the coherent peak, depends on the transport mean free path t and the absorption length of the light in the medium. The angular width of the coherent peak can be directly related to $l_t$ by $\lambda/(2\pi l)$, where $\lambda$ is the wavelength.

Paper has internal structure from fibers that scatter the light and contains local information of this nm structure and variation which is revealed in the spatial frequencies spectrum from the paper (box, money bills, envelope) and gems (diamonds) from defects to have unique spatial frequencies as a code number to uniquely locate and detect the particular package, bill, paper goods without a number as used today and certify a paint and a diamond using its spatial frequency spectra. Gems can be code for spatial frequency using nm structures of native or induced. Money can be coded with spatial variations of fiber array to scatter light to give spatial information about the material.

The method and apparatus of the invention can be used to ascertain the surface spatial properties of opaque materials (by reflection) as well as the spatial properties of internal structures in transparent materials (by transmission).

BRIEF DESCRIPTION OF THE DRAWINGS

The accompanying drawings, which are incorporated in and form a part of the specification, illustrate preferred embodiments of the present invention, and together with the description, serve to explain the principles of the invention, in which:

FIGS. 4(a)-4(d) are spatial frequency images of (a) normal, (b) CIN 1, (c) CIN 2, and (d) CIN 3 tissues, respectively, using 2D Fourier transform of their corresponding confocal microscope images; and FIGS. 4(e)-4(h) are plots obtained by the digital spatial cross section frequency distributions at the most dominant frequency along horizontal directions in FIGS. 4(a)-4(d), respectively;

FIGS. 6(a) and 6(b) show experimental results of spatial frequency distribution as painting fingerprints using Fourier optics and show speckle images taken from different paintings from the same artist; FIGS. 6(c) and 6(d) are FFT of FIGS. 6(a) and 6(b), respectively; FIGS. 5, 6(e) and 6(f) are spatial frequency distributions along x-axis in FIGS. 6(e) and 6(d); and FIGS. 6(g)-6(l) are similar to FIGS. 6(a)-6(l) and show the same experimental results from another artist using different paintings.

DETAILED DESCRIPTION

The invention will be illustrated by two examples— tissues and art forms that demonstrate the method using a Spatial Frequency Spectrometer.

Figures 1A, 1B, 1C, 1D:
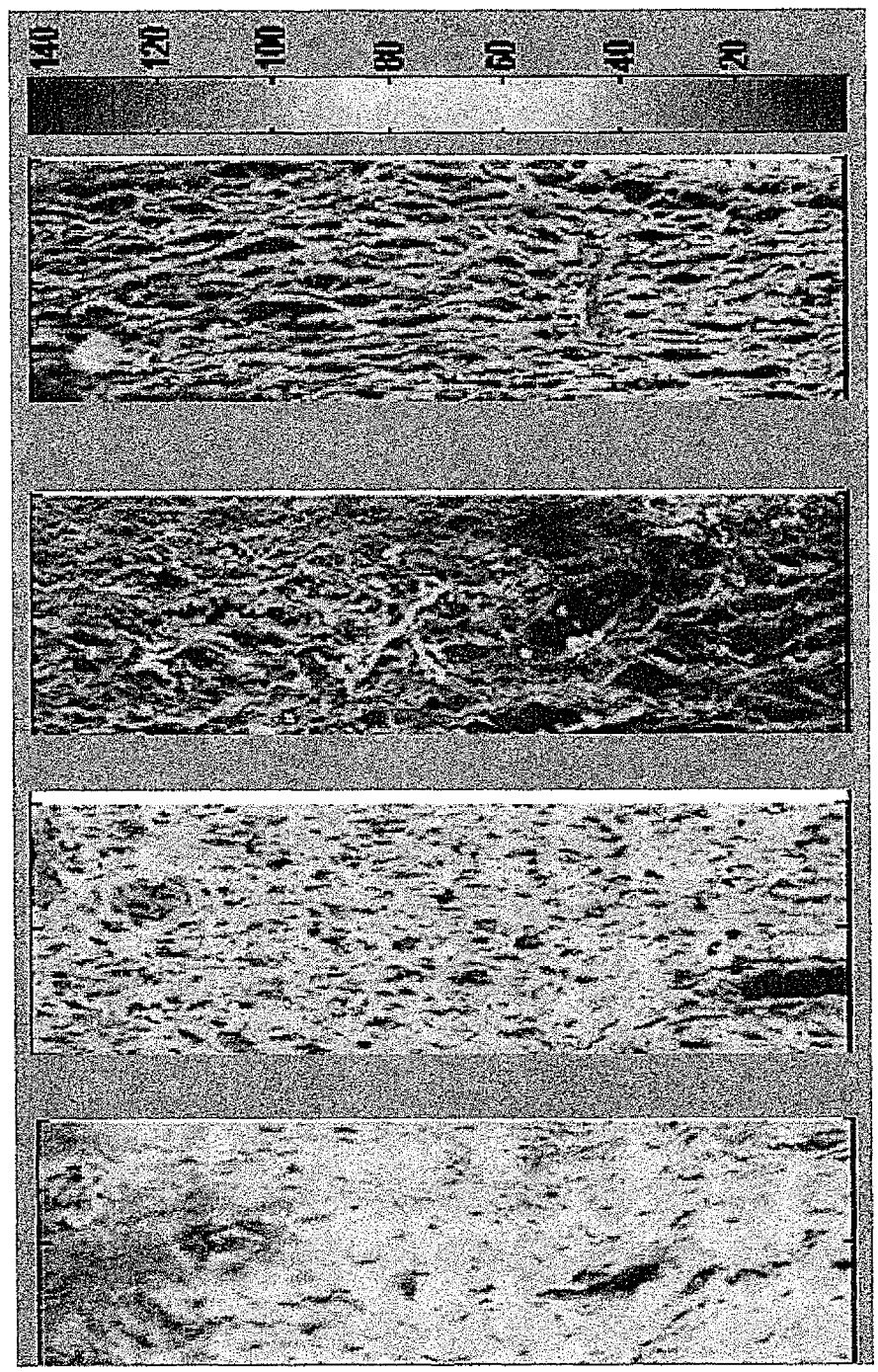
FIGS. 1(a)-1(d) are cropped portions of typical confocal microscope images stroma of (a) normal, (b) CIN 1, (c) CIN 2, and (d) CIN 3 tissues respectively.

A set of 5 μm thick tissue sections of human cervix of normal, CIN 1, CIN 2, and CIN 3 tissues stained by H&E is used in this study. The spatial frequencies of these tissues images were measured and analyzed. Their images were taken by a confocal microscope (Leica TCS SP5) and shown in FIGS. 1 (a), (b), (c), and (d) for the normal, CIN 1, 2, and 3 cervical tissues, respectively.

Figure 2:
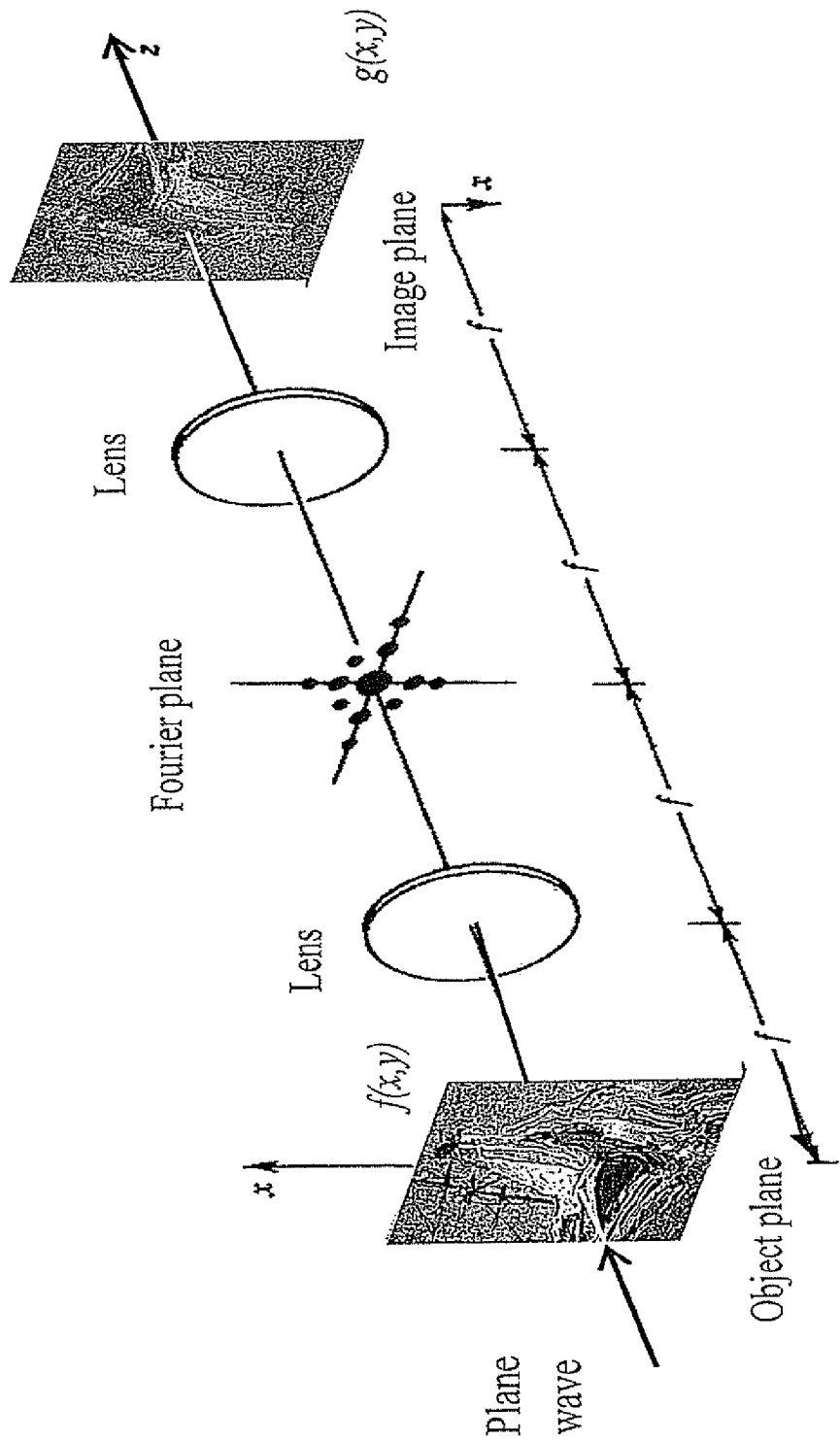
FIG. 2 is a schematic diagram of a 4-F optical system.
Figure 2A:
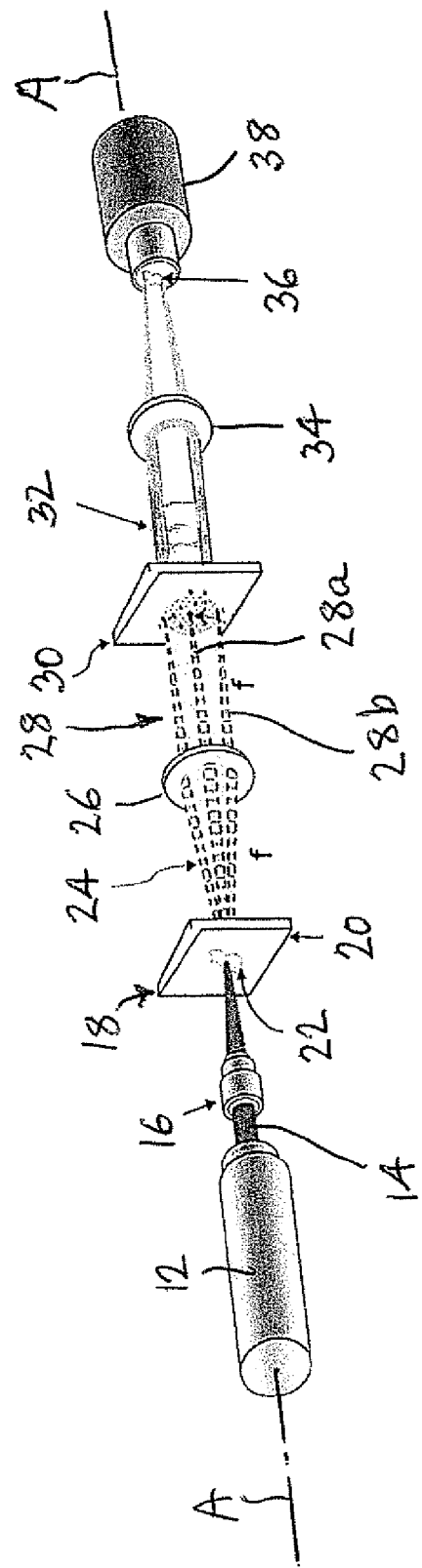
FIG. 2(a) is similar to FIG. 2 showing the optical components used to implement the invention.
Figure 2B:
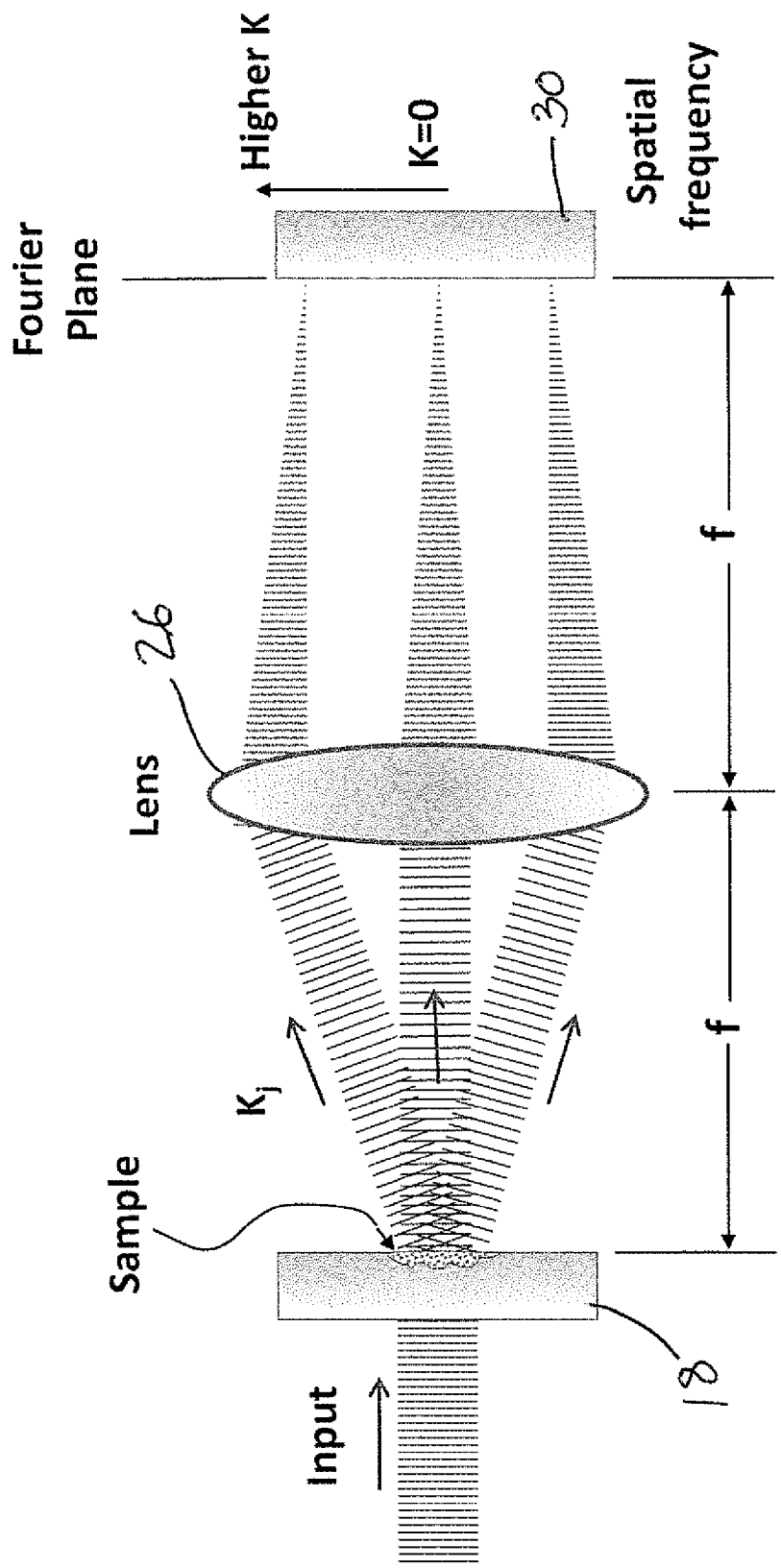
FIG. 2(b) is a more detail light ray diagram shown in FIGS. 2 and 2(a) illustrating the conversion of a light beam to a spatial frequency distribution by the system to reflect the spatial properties of s sample within a transparent medium.

A 4-F optical system shown in FIGS. 2-2(b) is used to record the Fourier images of the art form. As shown in these Figures, to record the Fourier Transform (FT) of an object, the object is placed at a distance f away from the lens. The image is recorded on a CCD camera at a distance f away from the lens to display the spatial frequency in the FT plane associated with the art form.

Referring specifically to FIG. 2(a), a spatial frequency spectrometer or optical system in accordance with the invention is generally designated by the reference numeral 10. The system 10 includes a laser 12 for issuing a beam 14 transmitted along a direction defining an axis A. The beam 14 is directed at a sample 18. In one example, the sample 18 is a slide 20 that is generally transparent and internally bears a structure 22 the spatial frequency of which is to be analyzed to determine its structural properties. In the example shown, the internal structure are cells. However, any internal structure can be placed in the object plane. In the example illustrated, the slide 20 is transparent and, thus, the light is mostly transmitted therethrough as modified by the internal structure(s). The scattered beams are then transmitted through a lens 26 that generates a visual pattern that is a function of the spatial frequencies. Thus, the beam 20a generally directed along the axis A, is a zero spatial frequency while higher spatial frequencies 28b are arranged as n-beams at the Fourier plane 30. The resulting beam 32 emanating from the plate 30, at the Fourier plane contains all the spatial frequencies which are, in turn, at least partially focused by a lens 34 to assume a composite spatial frequency image 36 at a distance f from the lens 34. A digital camera 38 receives the image 36 that can convert the light image into a spatial frequency distribution including the zero frequencies along the axis and higher order frequencies off the axis A. The beam 14 need not be collimated light and any light beam 14 can be used. It will be understood that the apparatus can be used to ascertain the properties of both internal and external structures at the object plane. In the example shown, the slide 20 is transparent so that the light continues to travel along the axis A. To the extent that the sample 18 is opaque and does not transmit light, the same is similar approach can be taken by reflecting the beam of light off of sample 18. The setup shown in FIG. 2(a) is ideal for ascertaining the characteristics of a sample that transmits the light beam, as suggested. However, to examine or compare works of art, which do not transmit a light beam, the light beam needs to be reflected, preferably at an angle in relation to the axis A where components similar to lens 26, Fourier plate 30, lens 32 and a digital camera 38 can be positioned on the same side as the laser 12. While a digital camera 38 has been shown to capture and display the spatial frequencies, any suitable light sensor, such as a CCD or CMOS or any other digital device that can receive and display the spatial frequencies can be used.

In FIG. 2(b) the input light beam 14 is dispersed into multiple spatial frequencies where $K_j$ is the $j^{th}$ spatial frequency. The distribution at the Fourier plane reflects the dispersion of the spatial frequencies, where K=0 corresponds to the zero spatial frequency, along the axis, and higher spatial frequencies $K_j$ are offset from the axis.

One application is to analyze the brush strokes and style of an artist form unique spatial frequency distribution as the fingerprints of the painting. The spectrum of the painting has a unique set of high and low spatial frequencies, analogous with light spectrum from scattering from molecules with Raleigh, Brillouin, and Raman spectra.

Basic Theory

Figure 3A:
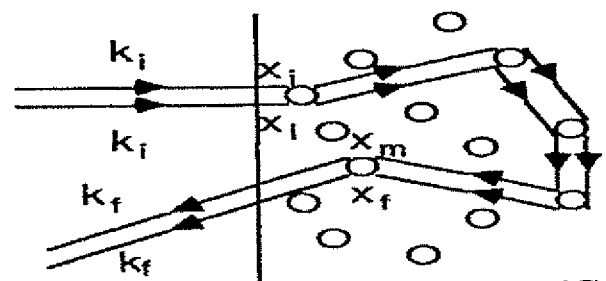
FIGS. 3(a)-3(c) are light scattering patterns through a series of scatterers: (a) $x_i = x_i$; $x_f = x_m$; (b) $x_i = x_m$; $x_f = x_i$; and (c) others.
Figure 3B:
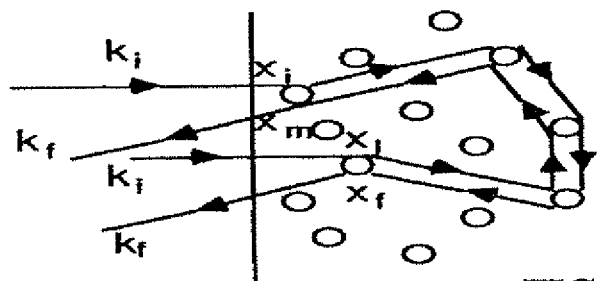
Figure 3C:
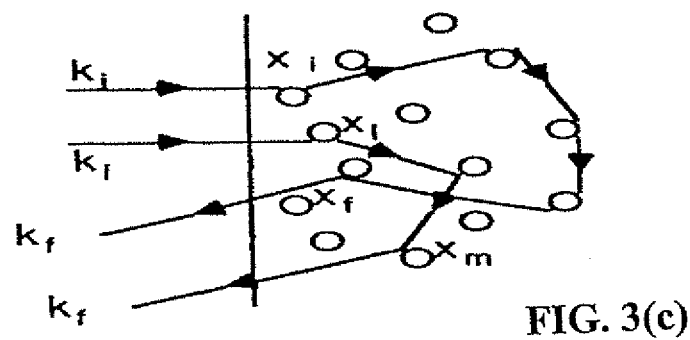

When light enters a disordered medium and structured medium, it is inevitably scattered and/or glows with information within the output light. The transport of light in this medium depends on the following parameters: the scattering cross section σ, the albedo $W_0$, the scatterer number density n, and the transport mean free path l. Until recently, an important property of light transport has not been seriously taken into consideration; that is, light propagation in a random medium possesses the property of time reversal symmetry. The intensity of light scattered from a random medium involves a solution to the wave equation. The solution consists of three terms representing the scattering in FIGS. 3(a), (b), and (c), respectively. The first term is a purely diffuse scattering, and there is no angular dependence on the scattered intensity. The second term (shown in FIG. 3(b)) has taken the time reversal symmetry into account and holds as long as the time reversal symmetry is not destroyed along the scattering trajectories, which is true in most media except in the presence of a magnetic field, where the time reversal symmetry is destroyed. This term contributes to the coherent interference in the backward direction (weak localization), and the scattered intensity is determined by the phase shift. This coherent interference is an important interference that exists for light scattering from dense random media. The last term [FIG. 3(c)] describes completely random scattering. This gives rise to a large intensity fluctuation and is normally observed in laser scattering from solid random media. In the case of particles dispersed in liquid, the random Brownian motion of the suspended particles acts as a natural dynamics for many different configurations of particle distribution. For micro-size latex beads suspended in water, the time taken for rearrangement is of the order of milliseconds. Thus, in the CW laser experiment, the observed angular intensity profile of light scattering from the random media is rather smooth.

The profile of the angular distribution of scattered light intensity about the backward direction, known as the coherent peak, depends on the transport mean free path t and the absorption length $l_a$ of the light in the medium. The angular width of the coherent peak can be directly related to $l_t$ by $\lambda/2\pi l_t$, where $\lambda$ is the wavelength. The line shape of the coherent peak can be quantitatively described by $$\alpha(\theta) = \frac{3}{16\pi}\left\{1 + 2\frac{z_0}{l_t} + \frac{1}{(1+ql_t)^2}\left[1 + \frac{1-\exp(-2qz_0)}{ql_t}\right]\right\}, \quad (1)$$

where $\theta$ is the angle of the scattered light measured from the exact backward direction, $q=2\pi\theta/\lambda$, and $z_0$ is determined by the boundary condition (in a plane interface, $z_0=0.71$).

A material, photo, scene or art form is a 2D intensity distribution. Across the screen there are various points of irradiance variation from local structures. The salient feature in the teachings is the use of Fourier transforms to detect spatial variations in a material. For example the painting can be transformed into a series of sinusoidal functions, like any function can be represented by Fourier series consisting of Fourier components with different frequencies. An object in space can be represented by a Fourier Transform (FT) by its spatial frequency spectrum.

The 2D Fourier transform of electric field $\epsilon$ in space $E(x,y,z)$ emitted from an object is given by:

$$\varepsilon(x, y) = \frac{1}{(2\pi)^2}\int\int E(k_x, k_y)\exp(-i(k_x x + k_y y))dk_x dk_y \quad (2)$$

and $$E(k_x, k_y) = \int\int \varepsilon(x, y)\exp(-i(k_x x + k_y y))dxdy \quad (3)$$

where $k_x$ and $k_y$ are angular spatial frequencies. The $k_x$ and $k_y$ spatial frequencies make up and are needed to form the object in space at (x,y). A lens of focal length f is used to take a FT of object to obtain its spatial frequencies associated with the art form. An object has unique set of spatial frequency as its fingerprint.

The light intensity distribution in an image can be expressed as 2D functions $f(x,y)$ in spatial coordinates (x,y), which describe how intensities or colors values (in our case) vary in space. In general case, a Fourier series representation of a 2D function, $f(x,y)$, can be expressed as [5]:

$$f(x, y) = \sum_{u=0}^{\infty}\sum_{v=0}^{\infty}a_{u,v}\cos\left[\frac{2\pi ux}{L_x} + \frac{2\pi vy}{L_y}\right] + b_{u,v}\sin\left[\frac{2\pi ux}{L_x} + \frac{2\pi vy}{L_y}\right], \quad (4)$$

where u and v are the numbers of cycles fitting into one horizontal and vertical period of $f(x,y)$ having a period $L_x$ and $L_x$ in the x and y directions, respectively. Another representation is based on spatial frequencies of color variations over the image plane [1, 5]. Converting the 2D spatial function $f(x,y)$ into the 2D spectrum $F(u,v)$ of spatial frequencies, Forward Fourier Transform (FFT) is usually-used mathematical tools without loss of information. In general case, Fourier series of $f(x,y)$ should be considered as infinite pair of 2D arrays of coefficients. In the algorithms of digital signal processing (DSP), the Discrete Fourier Transform (DFT) of a finite extent N×N sampling of 2D intensity distribution is usually used [5]:

$$F(u, v) = \frac{1}{N}\sum_{x=0}^{N-1}\sum_{y=0}^{N-1}f(x, y)\left[\cos\left(\frac{2\pi(ux+vy)}{N}\right) + j\sin\left(\frac{2\pi(ux+vy)}{N}\right)\right]. \quad (5)$$

Equation (2) can be simplified as [6]:

$$|F(u,v)| = \sqrt{R^2(u,v) + I^2(u,v)} \quad (6)$$

where R(u,v) and I(u,v) are the real and imaginary parts, respectively; and important information such as the magnitude spectrum, |F(u,v)| cart be Obtained by calculating each complex coefficient F(u,v) [6]:

$$F(u,v) = R(u,v) + jI(u,v) = |F(u,v)|e^{-j\phi(u,v)}. \quad (7)$$

The Fourier components are determined from a material's surface or within materials such as tissues as a new pathology, art forms to reduce forgeries, money bills to code from fiber structure and variations, mail to secure envelope, quality of gems such as diamonds to certify perfection from defects. The display of the spatial frequency forms the heart of the Spatial Frequency Spectrometer for structure material analysis in analog to optical spectrometer to give molecular components of materials.

Two detail examples are given next:

Detail Results of Fourier Data of Spatial Frequency of Tissue Types—a New Pathology Tissues: In order to obtain the information of discontinuity and aperiodicity for cervical tissue at different UN grades, the DFT of data in FIG. 4 was achieved using Origin 8.5 built in function by sampling N=256 of pixel. The 2D amplitudes spectra of normal, CIN 1, 2, and 3 cervical tissues are shown as FIGS. 4(a)-4(d), respectively. For the visual purpose, 2D amplitude spectra shown in FIG. 4 were obtained with the truncated linear mapping of the initial amplitudes and the logarithms of amplitudes [7] in the color range of [0, 255].

The Fourier spatial frequencies are plotted in FIGS. 4(e)-4(h) are typical results of 2D DFT that the dominant spatial frequency is at the origin—zero frequency (u=0, v=0), and increases in all directions away from the center [8]. However, the salient difference among FIGS. 4(a)-4(d) are observed that more higher frequency components exist in CIN tissues than those in normal tissue, as well as those in higher grade CIN tissue than those in lower grade CIN tissue.

The salient features display in FIG. 4 to diagnose tissue are as follows: for the normal tissue and the lower grade CIN tissues, the lower frequency amplitudes mostly dominate over the mid-range and high-frequency ones, but the mid-range and high-frequency amplitude spectrum can be perceived more and more clearly with the evolution from normal to CIN, and development from low grade to high grade CIN. These differences among the different types of tissues can be more clearly seen from their spatial frequency distributions at the same pixel row crossing the areas of the most dominant frequency along horizontal direction. FIGS. 4 (e), (f), (g), and (h) show the digital spatial cross section frequency distributions of the FIGS. 2 (a), (b), (c), and (d), respectively. The spatial frequency obtained by the DFT of different types of images shows that the higher grade of CIN tissue, the more and the wider spatial frequency range is. This observation is in good agreement as the cervical tumor development [1]. There is more disorder in the higher grade cancers than normal.

Depending on features or factors such as the location of the infection, CIN can start in any of the three stages, and can either progress, or regress [1]. CIN 1 is the least risky type, confined to the basal ⅓ of the epithelium; CIN 2 is the moderate neoplasia confined to the basal ⅔ of the epithelium; and CIN 3 is the severe one spanning more than ⅔ of the epithelium, and maybe involving the full thickness [1]. The lesion of CIN 3 may sometimes also be referred to as cervical carcinoma in situ [1]. The patterns of normal and low grade CIN tissues consist of evenly placed uniform epithelia cells supported by a well-structured surrounding extracellular matrix (ECM), which is composed mainly by collagen [4]. With grade advances, the tumor cells proliferate thus degrade ECM and cause the loss and randomness of collagens [4].

Outcome of Method: Tissues

Since our images example for tissue were taken in the stromal region of cervical tissues, the collagen in the normal tissue is more ordered in layers and uniform in shape and size while those in CIN precancer tissues are aperiodic random, anti-symmetrical, different sizes, and disordered in structure with more structure parameters. This is the reason why higher grade CIN tissues have wider spatial frequency range in comparison with lower grade CIN and normal cervical tissues.

Figures 5A, 5B:
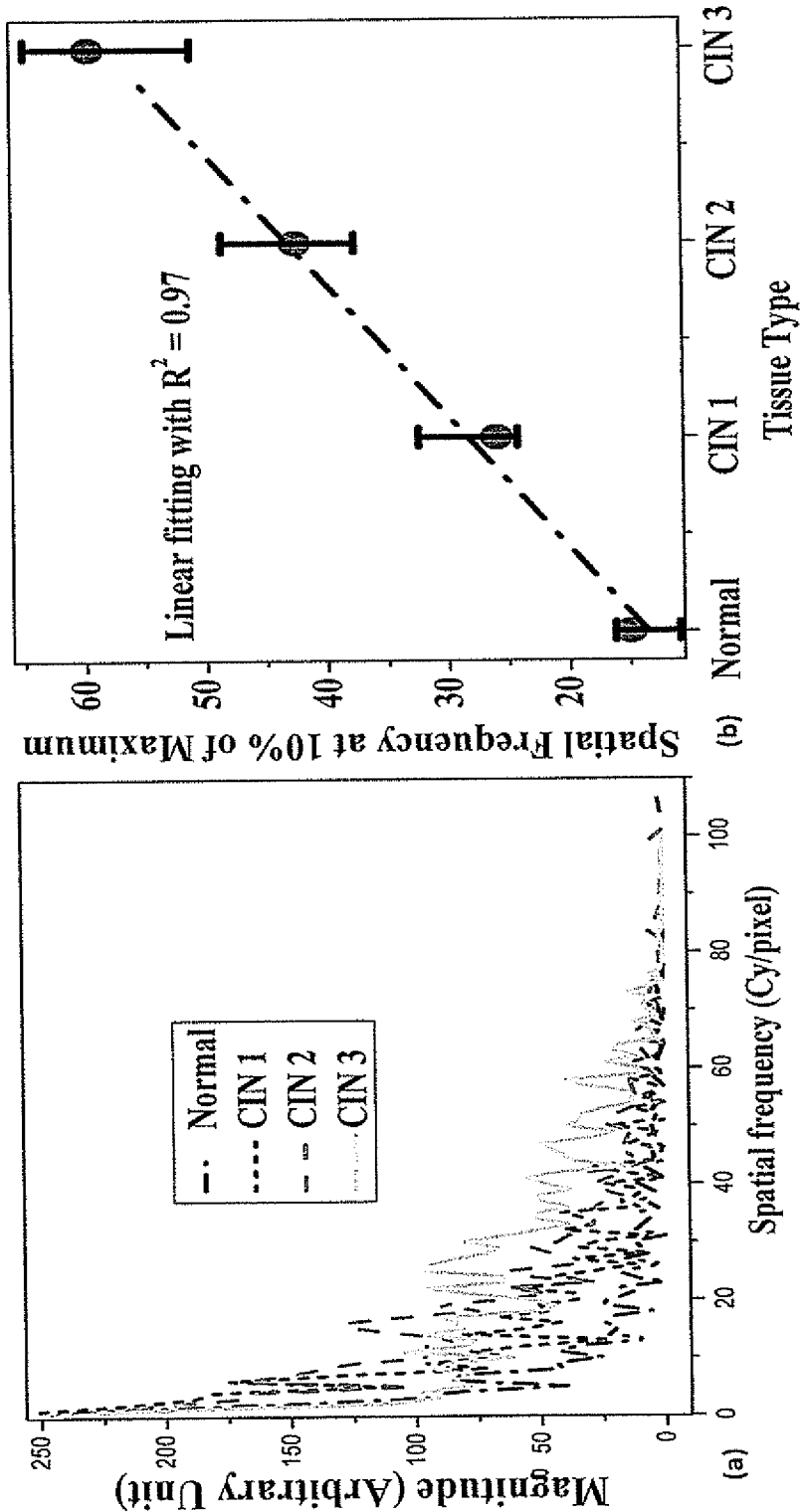
FIG. 5(a) shows plots comparing the differences of spatial frequency distributions of normal (dash-dot), CIN 1 (short dash), CIN 2 (dash), and CIN 3 (solid) tissues.
FIG. 5(b) is a plot showing the levels of "whitening of the spatial frequency" as a function of normal and CIN grade shown in FIG. 5(a)

The differences of spatial frequency distributions among these tissues with different risk levels may be directly exposed by plotting all their spatial frequencies in same condition. FIG. 5(a) shows spatial frequency distributions of normal (dash-dot), CIN 1 (short dash), CIN 2 (dash), and CIN 3 (solid) tissues, respectively. It can be seen from FIG. 4 the increase of spatial frequency range from normal to CIN tissues, and from low grade CIN to high grade CIN tissues. In spectral analysis, the expanding the range refers to more frequency components. The wider spatial frequencies of CIN type tissues provide diagnostic criteria for grading CIN tissues—a new quantitative histology.

In order to evaluate this potential, FIG. 4(b) shows the width of range for the spatial frequency from the full maximum decreasing to 10% of the maximum as a function of normal and CIN grade. It is important to note that the "whitening of the spatial frequency signal" exhibited a monotonous growth with the CIN grades. It could be seen that there is a parallelism between CIN grades [9] and levels of "whitening of the spatial frequency" [5]. This linear dependent property can be schematically shown as the dash dote line in FIG. 5(b), which can be characterized by correlation coefficient: $R^2=0.97$ using linear regression analysis of these two groups of data. (The normal tissue is taken as grade 0). An attempt was achieved to establish parallelism between CIN grades and levels of "wider" in our preliminary study.

This investigation on a set of human normal, CIN 1, CIN 2, and CIN 3 cervical using spatial Fourier analysis of their confocal microscope images shows potential to obtain information from the spatial frequency distributions of these samples. With the evolution from normal to CIN tissues and the development from low grade to high grade CIN tissues, the "wider the spatial frequency" was observed. This can be understood by more ordered layers and uniform collagen of shape and size in the normal and low grade CIN tissue, but periodic random, anti-symmetrical, different sizes, and disordered in structure of collagen in high grade CIN tissue. This study in vitro could discriminate the normal and three grades CIN tissues. Further based on "wider spatial frequency" as a function of CIN grade, a spatial spectral grading in parallels with CIN grading could be established with the linear fit in excess of 0.90. This new approach to use spatial frequencies to diagnose tissue change offers a new armamentarium in optical biopsy and pathology to create a better quantitative histology.

Detail Example Results of Fourier Data of Spatial Frequency of Art Forms

Art forms: To test this principle of spatial frequency of FT of artist art works (paintings), we measure the FT spectra using 632.8 nm light on paintings from different artists. The spatial frequencies will depend on the incident wavelengths since the key lengths of absorption and scattering depend on wavelengths. The use of SC and selection of FT at ultraviolet (UV), visible and near infrared (NIR) can obtain the unique fingerprints of the paint by the spatial frequency spectra. Also, LED and lasers can be used as the source. Experimental results of the FT from several paintings were measured to demonstrate the potential of the spatial frequencies. FIG. 6 shows preliminary results of spatial frequency distribution of several painting provided from Art Department students at City College of CUNY as painting fingerprints using Fourier optics of art forms from two artists. FIGS. 6 (a), (b), (g) and (h) are spatial frequency images taken using the setup shown as FIG. 2 using He—Ne laser. FIG. 6(c)-6(h) are two dimensional Fourier transform of FIG. 6(a)-6(h). Notice the similar spatial distributions from different art forms of the same artist, but different spatial patterns from different artists recovered by the Fourier transform algorithm shown by FIGS. 6(c)-6(j), respectively. This can be made more clear by plotting the spatial pattern of (c), (d), (i) and (j) as (e), (f), (k) and (l), respectively. Notice the spatial frequencies of the painting of a scene are similar of same artist and different for different artist. We can see the bell shape for one artist and exponential shape from another.

The measurements also show much different intensity between different paintings. These differences are caused by the different pigments that have different absorption length $l_a$ and transport lengths lt. The absorption length $l_a$ is the distance over which the light propagates in the medium before it is absorbed. This length depends on the chemical composition of the medium i.e., the absorption cross section and the concentration of the absorbing molecules present in the medium. Thus a change in absorption length indicates a change in pigment composition of the painting.

While the invention has been described in detail and with reference to specific examples and the embodiments thereof, it will be apparent to one skilled in the art that various changes and modifications can be made therein without departing from the spirit and scope thereof.

REFERENCE

[1] Joseph Goodman, "Introduction to Fourier Optics, Third Edition," Roberts & Company, ISBN 0-9747077-2-4, Copyright @ 2005.
[2] Barbara Hoffman, John Schorge, Joseph Schaffer, Lisa Halvorson, Karen Bradshaw, F. Cunningham, "Williams Gynecology, Second Edition," McGraw-Hill Professional, ISBN 978-0-07-171672-7, Copyright @ 2012.
[3] Jaidip Jagtap, Pankaj Singh, Chayanika Pantola, Asha Agarwal, Kiran Pandey, Asima Pradhan, "Study and discrimination of human cervical tissue images through multifractal analysis,"
[4] Yang Pu, W. B. Wang, Yuanlong Yang, and R. R. Alfano, "Stokes shift spectroscopy highlights differences of cancerous and normal human tissues," Opt. Lett., 37(16), 3360-3362 (2012).
[5] Nick Efford, "Digital Image Processing: A Practical Introduction Using Java™," Pearson Education, Addison-Wesley, ISBN-13: 9780201596236, Copyright ©2000
[6] B. E. A. Saleh and M. C. Teich, "Fundamentals of Photonics, Chapter 2, Fourier Optics," John Wiley & Sons, Inc., ISBN 978-0-471-35832-9, Copyright @ 2007
[7] S. Alexandrov, S. Uttam, R. K. Bista, Y. Liu, "Spectral encoding of spatial frequency approach for characterization of nanoscale structures," Appl Phys Lett., 101(4), 033702 (2012).
[8] S. Chung, G. Legge, and B. Tjan, "Spatial-frequency characteristics of letter identification in central and peripheral vision," Vision Res., 42(18), 2137-152 (2002)
[9] L. Cherkezyan, H. Subramanian, V. Stoyneva, J. Rogers, S. Yang, D. Damania, A. Taflove, V. Backman, "Targeted alteration of real and imaginary refractive index of biological cells by histological staining," Opt. Lett., 37(10), 1601-1603 (2012)

What is claimed:
1. A method of detecting structure within a material comprising the steps of directing a beam of light along an optical axis; positioning the material along said optical axis for intercepting and scattering light from the material; positioning a first lens having a focal length f along said optical axis at a distance f from the location of the material for optically generating a Fourier spatial spectrum of the scattered light to display all spatial frequencies of the Fourier spatial spectrum at a Fourier plane; positioning a second lens having a focal length f along said optical axis spaced from said Fourier plane a distance greater than f; projecting said spatial frequencies at an image plane by said second lens; detecting said spatial frequencies at said image plane; comparing the spatial frequencies spectra to the spatial frequencies spectra of a reference structure; and determining the difference between the spatial frequencies of the material and the spatial frequencies of the reference structure to provide information about the structure of the material relative to the reference structure from the spatial frequency spectra.

2. A method as defined in claim 1, wherein said spatial frequencies of said spatial spectrum for the material are plotted in unit 1/L, such as $cm^{-1}$ or $mm^{-1}$.

3. A method as defined in claim 1, wherein the light is directed at a plane at an exterior surface of the material to characterize the structure at the exterior surface of the material.

4. A method as defined in claim 1, wherein the material is at least partially transparent and the light is directed at a plane spaced interiorly of an exterior surface of the material to cause light scattering at said interiorly spaced plane to characterize the structure at said interiorly spaced plane.

5. A method as defined in claim 1, wherein the light is generated by a laser.

6. A method as defined in claim 1, wherein a lens is used to form the Fourier transform.

7. A method as defined in claim 1, wherein a digital camera including a CCD, CMOS or other digital display is used to capture and display the Fourier spatial spectrum.

8. A method as defined in claim 1, wherein the material is selected from a group comprising art forms, painting, tissue types, paper, money bills, mail, package tracking, gems quality, particular diamonds, signatures, coding limits, and security.

9. A method as defined in claim 1, wherein human organ or skin tissue is detected for different stages of cancer to secure the health of patients by early cancer detection.

10. A method as defined in claim 1, wherein Fourier transform is applied to monitor the spatial frequency changes reflected by collagen fiber from normal cervical tissue to cervical intraepithelial neoplasia (CIN) including CIN1, CIN 2, and CIN 3 tissue.

11. A method as defined in claim 10, wherein the method detects aperiodic random, anti-symmetrical, difference sizes, and disordered in structure of collagen in high grade CIN tissue which is indicative of the degree of early cancer tissue in morphological change caused by cancer development.

12. A method as defined in claim 1, further comprising the steps of:
    (a) acquiring the fluorescence microscopic images of stromal region of cervical tissues to monitor the collagen in layers and uniform in shape and size in the normal tissue and different CIN grade tissues; and
    (b) using two dimensional (2D) Fourier transform to obtain 2D spatial frequency of the microscopic images to produce interpretable "fingerprints" of spatial frequency, which reflects more obviously the stages of CIN involved with tumor processes; and
    (c) establishing a parallelism between CIN grades and levels of "whitening", which is indicative of the degree of early cancer tissue in morphological change caused by cancer development.

13. A method as defined in claim 1, wherein cancer of skin, basal skin carcinoma (BCC), squamous cell carcinoma (SCC), and Melanoma of skin is detected from spatial frequencies of scattered spatial frequency light.

14. A method as defined in claim 1, wherein spatial frequencies from various tissues (arteries, Plaque, oral GI (gastrointestinal), GYN (gynecological reproductive system tissues), skin, brain, lung, liver, and kidney etc.) are measured and spatial frequency is used to determine the state of the tissue normal precancer and cancer spectra.

15. A method as defined in claim 1, wherein a Fourier transform spatial spectroscopy system is used for detecting art forgery.

16. A method as defined in claim 1, wherein supercontinuum pulses 400 nm to 2500 nm) or lasers are used to test art forgery by comparing art with materials with different structures.

17. A method as defined in claim 1, wherein a Fourier transform spatial spectroscopy system is used by scanning the surface of paintings and other textured art works to determine if the brushwork or the signature is done by the original artist.

18. A method as defined in claim 1, wherein spatial frequency is used to code gem stones and diamonds by detecting and comparing internal defects and spatial variations.

19. A method as defined in claim 1, wherein spatial frequency is used to code at least one of packages, mail and money.

20. An apparatus for detecting structure within a material comprising a source of light for directing a plane wave of light along an optical axis;
an object plane along said optical axis at which a material is positioned for analysis;
a first lens having a focal length f positioned along said axis for optically generating a Fourier spatial frequencies spectra at a Fourier plane spaced a distance f downstream from said first lens along said optical axis;
a second lens having a focal length f positioned along said optical axis at a distance greater than f downstream from said Fourier plane; a digital sensor along said optical axis downstream from said second lens for receiving said Fourier spatial frequencies spectra; means for comparing the spatial frequencies spectra to the spatial frequencies spectra of a reference structure; and means for determining the difference between the spatial frequencies spectra of the material and the spatial frequencies spectra of the reference structure to provide information about the structure of the material relative to the reference structure.

21. An apparatus as defined in claim 20, wherein a digital camera including a CCD, CMOS or other digital display is placed at said image plane to capture and display the spatial frequencies in the Fourier transform (FT) plane.

22. An apparatus as defined in claim 20, in combination with a spectral frequency spectrum microscope having an objective lens for imaging the spatial frequencies spectra at the fourier plane on to a CCD/CMOS detector of the size of the object on the range of one of micron mm to cm scale.

* * * * *